United States Patent [19]
Cummins

[11] Patent Number: 5,387,205
[45] Date of Patent: Feb. 7, 1995

[54] SELF-CONTAINED URINE COLLECTING DEVICE FOR USE BY FEMALES

[75] Inventor: Richard F. Cummins, Lawrence, Kans.

[73] Assignee: Rosinante, Inc., Eudora, Kans.

[21] Appl. No.: 135,907

[22] Filed: Oct. 13, 1993

[51] Int. Cl.6 ............................................... A61F 5/44
[52] U.S. Cl. .................... 604/329; 604/331; 4/144.3
[58] Field of Search ............................. 4/144.1–144.4; 604/328–331

[56] References Cited

U.S. PATENT DOCUMENTS

| | | |
|---|---|---|
| 3,727,244 | 4/1973 | Collins . |
| 3,776,235 | 12/1973 | Ratcliffe et al. . |
| 4,194,508 | 3/1980 | Anderson . |
| 4,309,779 | 1/1982 | Knight ................................. 4/144.3 |
| 4,610,675 | 9/1986 | Triunfol ............................... 4/144.3 |
| 4,681,572 | 7/1987 | Tokarz et al. . |
| 4,911,698 | 3/1990 | Wapner . |

FOREIGN PATENT DOCUMENTS 2070936 9/1981 United Kingdom ................ 604/329

*Primary Examiner*—Jerome L. Kruter
*Attorney, Agent, or Firm*—J. David Wharton

[57] ABSTRACT

A self-contained urine collecting devise usable by females comprising a bottle in the shape of a hollow body having a closed end and an opening disposed at the end of an upwardly extending neck. Joinable to the open end of the bottle is an interface shaped generally in the form of an oval ring comprising a protuberance at the lower portion of the interface, an opening defined by the upper portion of the interface, a peripheral lip disposed concentrically with respect to the opening, a lateral ridge positioned between the protuberance and the opening, and a lateral valley disposed coextensively to the ridge disposed between the ridge and the protuberance. In use, the protuberance is positioned slightly within the vaginal orifice to place the extralabially fitting opening of the apparatus directly in front of the urethral orifice. The peripheral lip conforms to the perineum of the user in complementary fashion to ensure a liquid tight seal. The lateral ridge and coextensive valley act in concert with the protuberance to further guard against urine and bacterial migration seepage into the vagina.

18 Claims, 2 Drawing Sheets

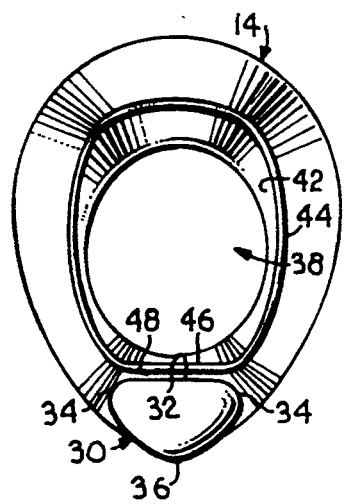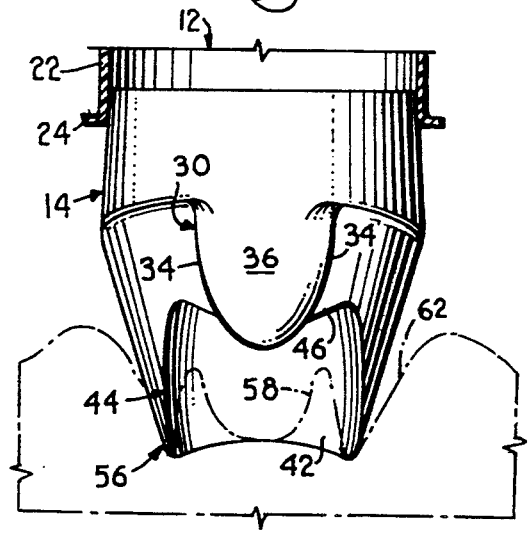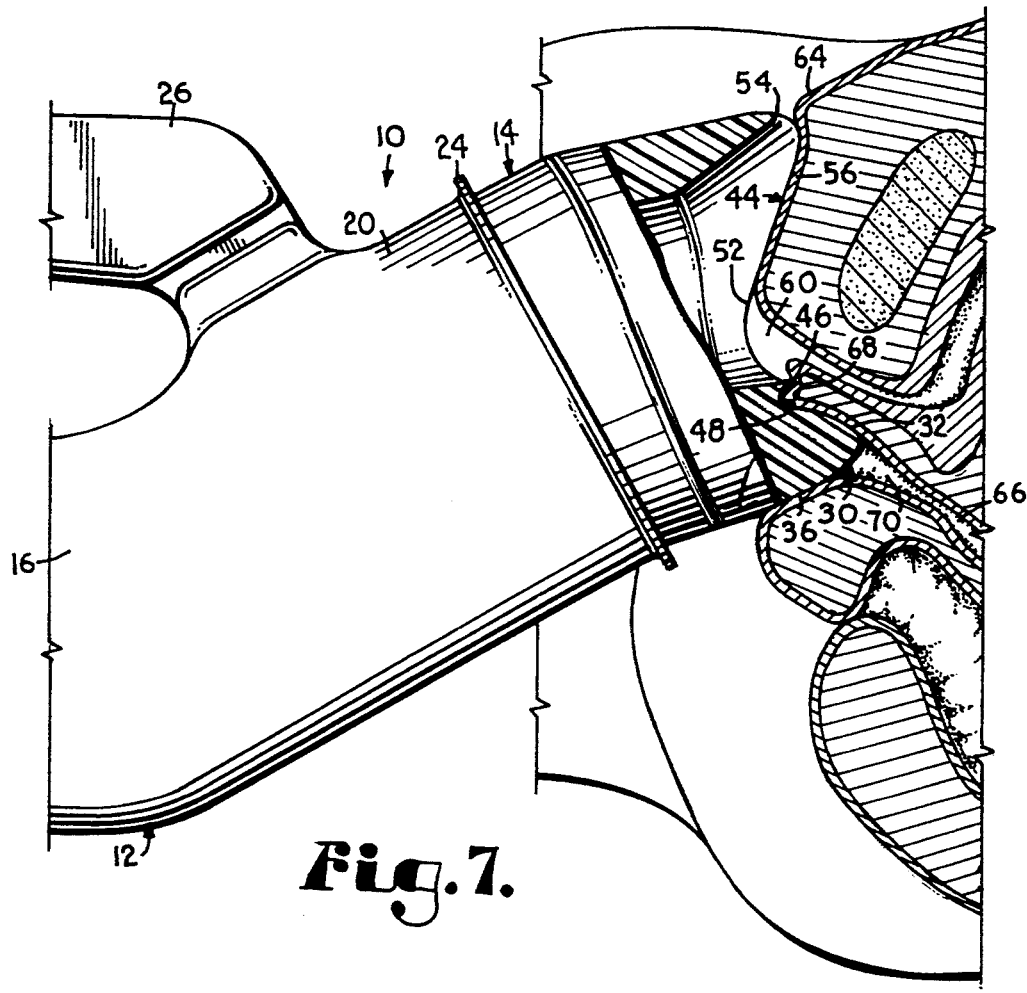

SELF-CONTAINED URINE COLLECTING DEVICE FOR USE BY FEMALES

BACKGROUND OF THE INVENTION

The present invention relates to a urine collecting device and more specifically, to an self-contained urine collecting device usable by females.

Urinals designed specific to the male anatomy have been well known and common in the art for many years. The technology utilized in designing and constructing male urinals is fairly rudimentary. Male urinals are basic in design largely because of the highly utilitarian capabilities of the multi-directional male urethra located within the penis. Moreover, due to the somewhat rare incidence of urinary tract infections in men, avoiding such infections has not been a male urinal design consideration.

Such mitigating features and conveniences are not present with respect to the female urinary system. The female urethral orifice is disposed at the surface of the perineum. The female anatomy presents no analogous penis-like appendage whereby urine flow can be directed into a receptacle. Consequently, any female urinal must be designed to accommodate a generally non-directable flow of urine.

In addition, bladder and other urinary tract infections are much more common with females. This is due, in part, because the female urethra is approximately one-third of the length of the male urethra. Thus, potentially infectious fomites must migrate only a short distance to reach the infection-prone bladder. Furthermore, the orifice of the female urethra is disposed in close proximity to the vaginal and anal orifices which are profuse with bacteria. This close proximity greatly increases the probability of organism migration into the urethral orifice. Therefore, a urine collection device designed for female users must also possess features that would inhibit or prevent urinary tract infections.

Similarly, because the female urethral orifice is disposed at the surface of the perineum, any urinal device must be designed to abut or adjoin the female user in a fluid-tight fashion to prevent the seepage of urine between the body and the device. It is important that such a urinal be formed to come into direct contact with the female body without undue discomfort, pain, or psychological stress.

Existing devices in the art address certain of the individual considerations set forth above. Notably, U.S. Pat. Nos. 3,776,235 and 4,194,508 disclose female urinary drainage devices which are employed for incontinence purposes. These inventions work well to divert urine from the female body by way of external tubes which empty into separate containers. However, the female user often experiences discomfort and inconvenience when using these devices. This is due to the operational placement of the devices which fit intravaginally and intralabially, respectively. Though workable for incontinence purposes, these devices can be uncomfortable for the female use because of their invasive nature.

Devices such as U.S. Pat. No. 4,911,698 isolate the urethral orifice from bacterial migration. In devices similar to this invention, an apparatus is inserted into the vaginal orifice and a hollow canal is placed intralabially over the urethral orifice. When used, urine passes directly into the hollow canal thereby avoiding vaginal contact altogether. The urine is then collected through a tube into a separate receptacle. Unfortunately, these devices are also devoid of considerations of user comfort and convenience.

In addition, simple bottle or jug-like apparatuses have been devised which accommodate both male and female users. With little attention to sanitation, user comfort, or spillage reduction, devices such as U.S. Pat. Nos. 4,309,779 and 3,727,244 essentially require the user to urinate into a receptacle. Formed mainly of rigid plastomeric materials, these urinals would appear to have been designed without the female user in mind. Though self-contained and of simple design, these urinals utilize extremely dated, if not primitive, technology to abruptly meet a very delicate need.

SUMMARY OF THE INVENTION

It is a primary object of the present invention to provide a manageable and convenient urine collecting device which is positioned extralabially on a female so that it is more comfortable than existing devices which must be positioned intralabially.

It is another object of the present invention to provide a female urine collecting device as described that prevents bacterial migration from the vagina and anus into the urethral orifice, thereby greatly reducing the incidence of urinary tract infections.

It is yet another object of the present invention to provide a female urine collecting device that comfortably yet substantially completely abuts the female user without undue discomfort or pain.

It is still another object of the present invention to provide a female urine collecting device that effectively receives the urine stream without spillage outside the device or seepage to the surrounding area of the user.

It is a further object of the present invention to provide a female urine collecting device that can be easily moved and manipulated by the user or a third party to allow for expedient and spill-free deployment in a multitude of conditions.

To accomplish these and other related objects of the invention, the present invention relates to a self-contained urine collection device for use by females. In the preferred form, it comprises bottle in the shape of an elongated hollow body with one end being closed and the other being open. The open end of the bottle extends upwardly with respect to the horizontal axis of the bottle, in narrowing fashion, to form a neck-like structure. At the mouth of the neck is disposed a user interface with dimensions specific for the female anatomy.

This female-specific interface is preferably formed in the general shape of an irregular oval ring but may be round. At the bottom of the interface is a protuberance extending outwardly preferably in the shape of a cone. The upward surface of the protuberance is preferably somewhat planar but may also be substantial curved.

In the upper portion of the interface is an opening through which a urine stream may be directed for entry into the hollow body. Disposed concentrically around the opening is a peripheral rim extending outwardly beyond the opening. The side portions of the rim are recessed in arcuate fashion thereby presenting a concave edge. The upper portion of the rim is also recessed in arcuate fashion to similarly form a concave structure. The arcuate side portions of the peripheral rim meet the arcuate upper portion to create outwardly extending contact surfaces near the upper corners of the interface.

Between the opening and the protuberance is a lateral ridge. The lateral ridge is preferably formed as a continuation of the peripheral ridge but may also be a distinct structure. An inwardly depressed coextensive valley is laterally disposed between the ridge and protuberance.

In use, the device is placed between the legs of the female user with the interface abutting the user's body. The peripheral rim conforms snugly but comfortably against the perineum of the user. The protuberance of the interface fits slightly inside the vaginal orifice in liquid-tight fashion. The opening of the interface is positioned over and around the labium minus at a position directly in front of the urethral orifice. The lateral ridge abuts and slightly depresses the perineal septal surface between the urethral and vaginal orifices thereby causing the septal tissue to protrude into the valley. Correct and stable alignment of the interface is maintained by the contact surfaces.

The device disclosed herein allows sanitary and spill-free urination by an upright, prone or supine female user while at the same time not causing discomfort or pain. The device is designed to be easily and quickly deployed by the user or a third party.

BRIEF DESCRIPTION OF THE DRAWINGS

In the accompanying drawings which form part of the specification and are to be read in conjunction therewith and in which like numbers have been used to indicate like parts in the various views:

FIG. 5 is an end elevation view of the user interface shown removed from the bottle;

FIG. 6 is a bottom plan view of the forward portion of the urine collecting device with portions of the bottle being shown in horizontal section and portions of the female anatomy being shown in phantom lines; and FIG. 7 is an enlarged fragmentary side elevational view of the urine collecting device positioned for use by a supine female, anatomical parts and a portion of the user interface being shown in vertical section.

DESCRIPTION OF THE PREFERRED EMBODIMENT

Figure 1:
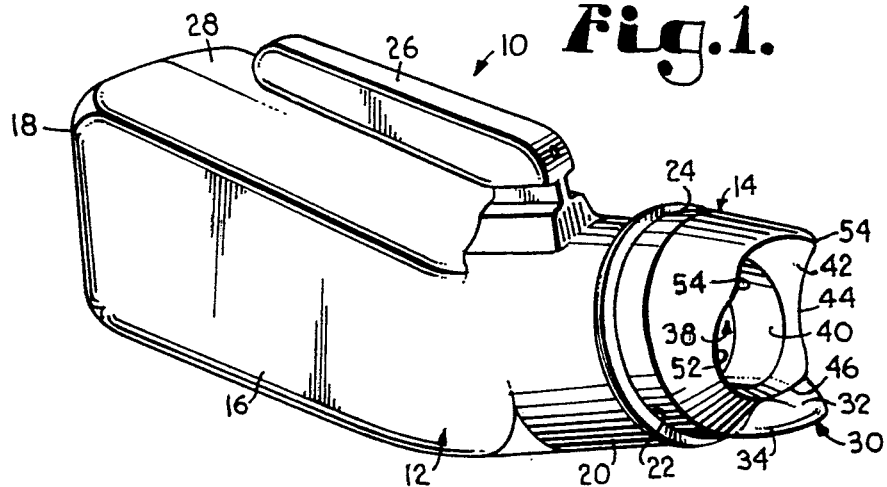
FIG. 1 is a side perspective view of a urine collecting device constructed in accordance with the present invention.
Figure 4:
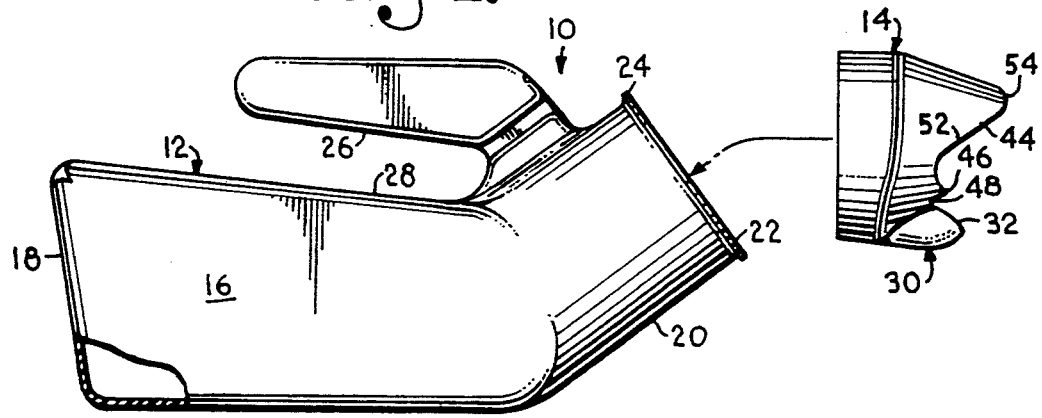
FIG. 4 is an exploded side elevation view of the urine collecting device with a portion of the bottle being broken away to illustrate its hollow construction.

Referring now to the drawings, and initially to FIGS. 1 and 4, a urine collecting device made in accordance with the present invention is represented broadly by the numeral 10. The device 10 utilizes a bottle 12 which temporarily stores the urine and a detachable user interface 14 which is shaped to anatomically conform to the female genital region.

Bottle 12 comprises an elongated hollow body 16 constructed of a hypoallergenic material, preferably translucent or transparent, possessing resilient characteristics which enable the device to withstand cleaning and sterilization after its use. The hollow body 16 has a closed, and relatively flat, end 18 and an opposite end which is open and extends upwardly to form a neck 20. Neck 20 terminates with a substantially round opening or mouth 22 and an outwardly extending rim 24.

Attached to or integrally formed with the neck 20 of the bottle 12 is a handle 26 which extends outwardly toward the closed end of 18 of the bottle 12. In the preferred form, handle 26 is spaced above the hollow body 16 of the device 10 and extends substantially parallel to an upper surface 28 of body 16. Other dispositions of handle 26, however, are also understood to be within the scope of the present invention.

Turning additionally to FIGS. 2–3 and 5–6, the user interface 14 will now be described in greater detail. Though the preferred embodiment utilizes a detachable interface 14, an integral construction is also envisioned and is within the ambit of the invention. As best shown in FIG. 5, a forward portion of the user interface 14 is preferably formed in the general shape of an irregular oval whose upper chordal diameter is greater than its lower chordal diameter. The rear portion of interface 14 is preferably of circular cross-section so that it conforms to the shape of the mouth 22 of bottle 12. The interface 14 seats within the mouth 22 by simply inserting the interface 14 into the mouth 22 where it is retained by frictional engagement. It will be understood that other suitable methods may be used to secure the interface 14 to bottle 12.

The interface 14 can be constructed of any hypoallergenic material capable of maintaining its shape, and desirably is also semi-malleable in character so that it is not abrasive to the user. The preferred embodiment of the interface 14 is constructed of a material capable of withstanding conditions necessary to sterilize and clean the interface 14 so that it may be reused.

The lower portion of the interface 14 includes forwardly extending protuberance 30 formed generally in the shape of a cone. The upper surface 32 of protuberance 30 is somewhat planar in the preferred embodiment of the invention and leads to rounded marginal edges 34. A rounded protuberance 30 is also anticipated and will be understood to be within the scope of the present invention. The bottom surface 36 of protuberance 30 is preferably rounded so that the protuberance has a generally oval-shaped cross-section with the larger dimension of the oval lying in a horizontal plane. It is preferred that the protuberance 30 be singularly fashioned with the other components of interface 14, though separate or modular compositions of the interface 14 are also envisioned as being within the ambit of the instant invention.

The user interface 14 further includes a substantially ovular opening 38 which is located in the upper portion of the interface 14 and allows urine to enter the device 10 for temporary storage in bottle 12. The opening 38 is positioned in interface 14 so that it is directly in front of the urethral orifice when the protuberance 30 is positioned within the vagina as described above. The opening 38 is of a size large enough to extend over and around the labium minus 58 of a female user. However, the opening is not so large as to allow open areas between the interface 14 and the perineum which could cause seepage of urine. Notably, since the opening 38 is sized to allow interface 14 to fit extralabially, the discomfort associated with the prior art is not encountered.

Figure 3:
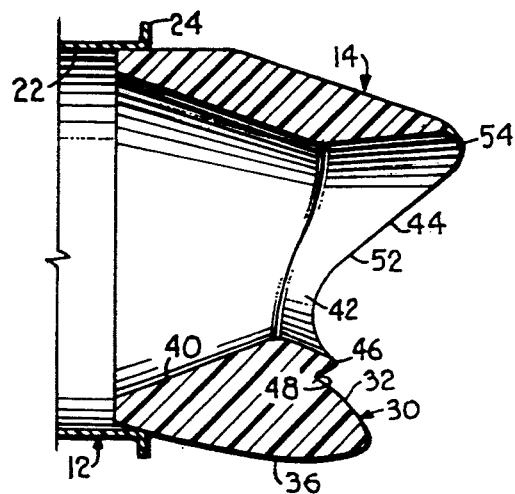
FIG. 3 is a side elevation view of the forward portion of the urine collecting device taken in vertical section along line 3—3 of FIG. 2 in the direction of the arrows.

As can best be seen in FIGS. 3–5, the opening 38 is defined by a rear inner wall section 40 and a forward inner wall section 42. Preferably, the rear inner wall 40 has an increasing diameter in the rearward 40 direction while the forward inner wall 42 has an increasing diameter in the forward direction and terminates in a peripheral lip 44. It is understood, however, that other orientations of the inner walls may prove workable and thus are within the scope of the present invention.

A lower portion of the peripheral lip 44 is preferably formed into a laterally extending ridge 46 which is positioned between the opening 38 and the protuberance 30. A lateral ridge 46 formed separate and distinct from peripheral lip 44 may also be used. This ridge 46 is generally planar and has substantially the same horizontal length as protuberance 30. The ridge 46 is spaced from protuberance 30 by a lateral valley 48 which is coextensive with ridge 46. In use, the lateral ridge 46 acts in coordination with the valley 48 and the protuberance 30 to insure a liquid-tight seal with respect to the vaginal orifice to effectively prevent any seepage of urine therein.

Figure 2:
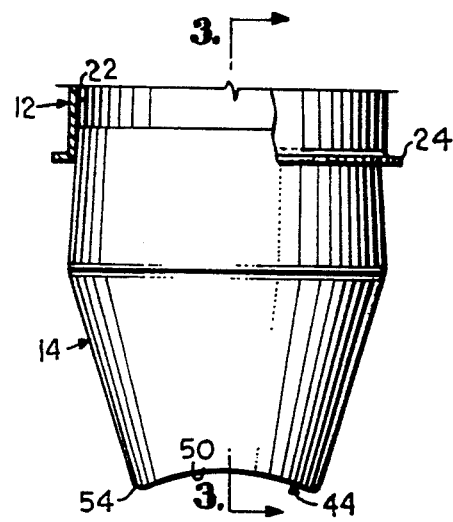
FIG. 2 is a fragmentary top plan view of a forward portion of the urine collecting device with portions broken away to show how the detachable user interface seats with the bottle portion of the urine collecting device.

As is best shown in FIGS. 2 and 6, an upper portion 50 of the peripheral lip 44 surrounding opening 38 is recessed in an arcuate fashion to provide a more anatomically conforming shape. Similarly, as seen in FIGS. 3 and 4, side portions 52 of the peripheral lip 44 extend rearwardly to provide a forward facing concave surface which facilitates engagement of the user interface 14 with the female anatomy. The arcuate shape of the upper and side portions of lip 44 results in the formation of forwardly extending contact surfaces 54. The location of these contact surfaces 54 above opening 38 increases the stability of the interface 14 when it is placed in engagement with the female anatomy.

Referring now to FIGS. 6–7, the urine collecting device 10 is shown as it would appear while in use. Broadly stated, the device fits up against in the perineum 56 of the female user in abutting fashion. The opening 38 of the user interface 14 fits generally around the labium minus 58 of the user and directly in front of the urethral orifice 60.

More precisely, the arcuate side portions 52 of the peripheral lip 44 conform anatomically to the profile of the anterior portion of the perineum 56 between the labium minus 58 and the labium majus 62. The conforming shape of the side portions 52 aids in preventing urine seepage outside the interface 14. In addition, because the side portions 52 of the interface 14 are specifically designed to conform to the user, the device 10 is much more comfortable to use than the existing art.

The upper portion 50 of the peripheral lip 44 is also designed for both utility and comfort. While in use, the arcuate upper portion 50 fits snugly against the inferior region of the mons pubis 64 of the user. Because the mons pubis is slightly convex in shape, the concave upper portion 50 abuts the user in complementary fashion, thereby encouraging a liquid tight seal. The recessed concave upper portion 50 also inhibits clitoral abrasion which further aids in promoting comfortable use of the device 10.

The contact surfaces 54 of the interface 14 serve chiefly to ensure accurate positioning of the device 10. When in use, the contact surfaces 54 of the interface 14 provide reference pressure points whereby the user can detect misalignment of the device 10 prior to urination. The contact surfaces 54 also increase the stability of the device 10 when engaged.

The protuberance 30 of the interface 14 is formed to fit snugly but slightly into the vaginal canal 66 of the user. The function of protuberance 30 is three-fold. First, it serves a positioning function to ensure the mouth 22 of the urine collecting device 10 is positioned directly in front of the urethral orifice of the female user. Second, it creates as a liquid-tight seal so that any urine that might seep from the user interface 14 cannot enter the vaginal canal. This function is enhanced by the horizontal oval shape of the protuberance 30 which causes lateral stretching of the vagina and encourages muscular contraction of the vaginal wall against the protuberance 30. It has been discovered that contraction of the vaginal wall onto the upper somewhat planar surface 32 of protuberance 30 provides an effective seal against entry of downwardly flowing urine into the vaginal canal 66. Third, though it extends only slightly into the vaginal canal, due to the muscular contractions encouraged by protuberance 30, it serves to hold the device 10 in place during urination.

When the device 10 is engaged, the lateral ridge 46 abuts the septal perineal surface 68 between the vaginal orifice 70 and urethral orifice 60. The lateral ridge 46 slightly depresses the septal tissue 62 which causes the posterior region of septum 68 to protrude into the lateral valley 48 of the interface 14 between the ridge structure 46 and the protuberance 30. The abutment between the septal tissue 68 and the ridge 46 and valley 48 of the interface 14 facilitates a gasket-like seal between the urethral orifice 60 and the vaginal canal 70 thereby prohibiting liquid communication.

When the device 10 is in place and the interface 14 fully engaged, the upright, prone, or supine positioned female user urinates into the opening 38 of the interface 14. Preferably, the neck structure 20 of the bottle 12 angles downward with respect to the urethral opening 36. Thus, the shape of the bottle 12 coincides with the incidence of the urine stream which flows outwardly from the urethral orifice 60 and downwardly in response to gravitational force. Because the neck 20 of the bottle 12 is disposed at an obtuse angle from the urine stream, excessive splashing of urine is eliminated.

After urination is complete, the device 8 is easily removed from the user and the urine conveniently discarded. The bottle 12 and interface 14 are then cleaned and sterilized so that the device 10 may be reused.

It will be appreciated that while the user interface 14 is specially adapted for use by a female, the opening 38 in the interface 14 is sized to accommodate use by a male. Alternatively, the interface 14 can simply be removed to allow the bottle 12 to be used as a urine collector by the male user.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A self-contained urine collecting device for use by females and adapted for placement at the user's urethral orifice, vaginal orifice, and septal tissue, said septal tissue being located between said urethral and vaginal orifices, said device comprising:

a hollow body, one end of said body being closed and an other end of said body being open;

an upwardly extending neck disposed at said open end of said body;

a mouth positioned in an essentially vertical plane disposed at an open end of said neck; and an interface extending from said mouth and comprising a protuberance extending outwardly from a lower portion of said interface and adapted for insertion into said vaginal orifice of said user to block entry of urine into said vaginal orifice, an opening defined by an upper portion of said interface and adapted for placement adjacent said urethral orifice of said user when the protuberance is inserted into the vaginal orifice, a laterally extending ridge disposed between said opening and said protuberance and adapted for positioning adjacent said septal tissue separating said urethral orifice and said vaginal orifice, and a lateral valley coextensive with said ridge and adapted for positioning adjacent said septal tissue separating said urethral orifice and said vaginal orifice, said valley acting in coordination with said ridge and said protuberance to provide a liquid-tight seal with respect to the vaginal orifice of the user.

2. The device as set forth in claim 1, including a handle extending outwardly from said neck and over said hollow body at an angle substantially parallel to an upper surface of said body.

3. The device as set forth in claim 2, wherein an upper surface of said protuberance is generally planar.

4. The device as set forth in claim 3, wherein said protuberance is of a size to fit snugly into a vaginal orifice to block entry of urine into said vaginal orifice.

5. The device as set forth in claim 4, wherein the opening is sized to surround a female user's labium minus and within the user's labium major.

6. The device as set forth in claim 5, wherein said lateral ridge is of a length substantially equal to or greater than a lateral diameter of said protuberance.

7. The device as set forth in claim 6, including a peripheral lip on said interface surrounding said opening and wherein said lateral ridge is formed as a continuation of said peripheral lip.

8. The device as set forth in claim 7, wherein said peripheral lip has recessed side portions and a recessed upper portion which define forward contact surfaces positioned above said opening.

9. The device as set forth in claim 6, including a peripheral lip on said interface surrounding said opening and wherein said lateral ridge is distinct from said peripheral lip.

10. A female urinal user interface for use with a urine receptacle and adapted for placement at the user's urethral orifice, vaginal orifice, and septal tissue, said septal tissue being located between said urethral and vaginal orifices, said interface comprising:

a generally ovular ring;

a protuberance extending outwardly from a lower portion of said ring and adapted for insertion into said vaginal orifice of said user to block entry of urine into said vaginal orifice;

an opening defined by the upper portion of said ring and adapted for placement adjacent said urethral orifice of said user when said protuberance is inserted into the vaginal orifice;

a peripheral lip disposed concentrically with respect to said opening;

a lateral valley disposed between said opening and said protuberance and adapted for positioning adjacent said septal tissue separating said urethral orifice and said vaginal orifice; and a lateral ridge coextensive with said valley and adapted for positioning adjacent said septal tissue separating said urethral orifice and said vaginal orifice, said ridge acting in coordination with said valley and said protuberance to provide a liquid-tight seal with respect to the vaginal orifice of the user.

11. The device as set forth in claim 10, wherein an upper surface of said protuberance is generally planar.

12. The device as set forth in claim 10, wherein said opening is sized to be positioned around a female user's labium minus and within said user's labium major.

13. The device as set forth in claim 12, wherein said lateral ridge is of a length substantially equal to a lateral diameter of said opening.

14. The device as set forth in claim 13, wherein said lateral ridge is formed as a continuation of said peripheral lip.

15. The device as set forth in claim 13, wherein said lateral ridge is distinct from said peripheral lip.

16. The device as set forth in claim 13, wherein said peripheral lip has an upper portion, two side portions and a forwardly extending contact surface disposed at each juncture of said upper portion and said side portions.

17. The device as set forth in claim 16, wherein said upper portion of said peripheral lip recesses rearwardly to form a concave ridge adapted to conform to a convex shape of an inferior region of the female user's mons pubis.

18. The device as set forth in claim 17, wherein said side portions of said peripheral lip recess rearwardly to form concave ridges adapted to conform to a profile of an anterior portion of the female user's perineum between the labium minus and labium majus.

* * * * *